US012734278B2

(12) United States Patent
Tran et al.

(10) Patent No.: US 12,734,278 B2

(45) Date of Patent: Sep. 15, 2026

(54) INTERPOSITIONAL PATCH SYSTEMS AND METHODS

(71) Applicant: Acuitive Technologies, Inc., Allendale, NJ (US)

(72) Inventors: Minh-Tuan Richard Tran, Ho-Ho-Kus, NJ (US); Michael P. McCarthy, Ho-Ho-Kus, NJ (US); Rui J. Ferreira, Livingston, NJ (US)

(73) Assignee: Acuitive Technologies, Inc., Allendale, NJ (US)

( * ) Notice: Subject to any disclaimer, the term of this patent is extended or adjusted under 35 U.S.C. 154(b) by 279 days.

(21) Appl. No.: 18/538,835

(22) Filed: Dec. 13, 2023

(65) Prior Publication Data

US 2024/0197966 A1 Jun. 20, 2024

Related U.S. Application Data

(60) Provisional application No. 63/432,547, filed on Dec. 14, 2022.

(51) Int. Cl.
*A61L 27/56* (2006.01)
*A61L 27/10* (2006.01)

(52) U.S. Cl.
CPC ............... *A61L 27/56* (2013.01); *A61L 27/10* (2013.01); *A61L 2430/10* (2013.01)

(58) Field of Classification Search
None
See application file for complete search history.

(56) References Cited

U.S. PATENT DOCUMENTS

| | | | |
|---|---|---|---|
| 7,964,206 | B2 | 6/2011 | Suokas et al. |
| 8,567,162 | B2 | 10/2013 | Bagga et al. |
| 9,308,076 | B2 | 4/2016 | Ringeisen et al. |
| 9,439,764 | B2 | 9/2016 | Shim et al. |
| 10,123,862 | B2 | 11/2018 | Landgrebe et al. |
| 10,279,074 | B2 | 5/2019 | Landgrebe et al. |
| 10,932,926 | B2 | 3/2021 | Bar et al. |
| 11,179,159 | B2 | 11/2021 | Cox et al. |
| 11,338,061 | B2 | 5/2022 | Bagga et al. |
| 11,491,264 | B2 | 11/2022 | Preiss-Bloom et al. |
| 11,654,214 | B2 | 5/2023 | Shah et al. |
| 11,672,540 | B2 | 6/2023 | Lorenzo et al. |
| 11,730,866 | B2 | 8/2023 | Preiss-Bloom et al. |
| 11,944,316 | B2 | 4/2024 | Connor |
| 2005/0043813 | A1 | 2/2005 | Kusanagi et al. |

(Continued)

OTHER PUBLICATIONS

International Search Report and Written Opinion from related International Patent Application No. PCT/US2023/083882 issued Apr. 1, 2024.

*Primary Examiner* — Dominic Lazaro

(74) *Attorney, Agent, or Firm* — McCarter & English, LLP

(57) ABSTRACT

A patch system and method for musculoskeletal repair is provided, the patch system including a patch that defines a patch thickness, the patch fabricated, in whole or in part, from a composition that includes a citrate polymer and a bioceramic filler, and wherein the patch defines a porosity gradient across the patch thickness. The patch may be defined by a plurality of patch layers, e.g., patch layers formed from a plurality of fibers, and first fibers associated with a first patch layer are non-aligned relative to second fibers in a second, adjacent patch layer.

21 Claims, 3 Drawing Sheets

(56) References Cited

U.S. PATENT DOCUMENTS

| | | | | |
|---|---|---|---|---|
| 2007/0224245 | A1 | 9/2007 | Ameer et al. | |
| 2016/0199541 | A1* | 7/2016 | Yang | C08G 63/52 528/291 |
| 2018/0228938 | A1* | 8/2018 | McGuire | A61L 27/3662 |
| 2023/0404773 | A1 | 12/2023 | Gantick et al. | |

* cited by examiner

INTERPOSITIONAL PATCH SYSTEMS AND METHODS

CROSS-REFERENCE TO RELATED APPLICATIONS

This application claims priority benefit to a U.S. provisional patent application entitled "Interpositional Patch Systems and Methods," which was filed on Dec. 14, 2022, and assigned Ser. No. 63/432,547. The entire content of the foregoing U.S. provisional patent application is incorporated herein by reference.

BACKGROUND

1. Technical Field

The present disclosure relates to interpositional patch systems and methods that include physical feature(s) produced from a citrate-based composite biomaterial to aid enthesis regeneration.

2. Background Art

The enthesis is a region of musculoskeletal structure that has been difficult to regenerate. One of the more commonly damaged regions is the rotator cuff. (See, e.g., Charousset C. et al., "Arthroscopic Repair of Full-Thickness Rotator Cuff Tears: Is There Tendon Healing in Patients Aged 65 Years or Older?" Arthroscopy: J. Arthroscopic Related Surgery 2010, 26 (3), 302-309.0 Many times, the rotator cuff is repaired by using only suture anchors, which has been clinically reported as having a high incidence of retears. This failure rate is attributed to the fibrous tissue (scar formation) that forms during the healing phase, preventing regeneration of the natural soft tissue enthesis. (See, e.g., Mather et al. "The Societal and Economic Value of Rotator Cuff Repair;" J. Bone Jt. Surg., Am. Vol 2013, 95 (22), 1993-2000.) In addition, current suture anchors only provide mechanical means to hold down soft tissue but do not provide structures or materials that aid in the biological healing process and regeneration of native tissue. A need exists for systems and methods that are effective in surgical treatment/repair that addresses the foregoing challenges.

SUMMARY

The present disclosure provides interpositional patch systems and methods that include physical/mechanical feature(s) produced from a citrate-based composite biomaterial to aid enthesis regeneration. The disclosed systems/methods include, inter alia, a biodegradable citrate-based scaffold that is effective in inducing natural healing and regeneration of tissue, including specifically enthesis tissue. In exemplary embodiments, the disclosed system is produced utilizing 3D printing equipment, thereby facilitating manufacture of a stratified, multiphasic construct that possesses mechanical and biochemical features more similar to the native transition zone.

In embodiments, the physical/mechanical feature(s) may be advantageously arranged/deployed as a gradient architecture through a patch system via a plurality of layers. For the patch surface to be clinically positioned closer to the bone site, the physical/mechanical feature(s) are designed to create/define a porosity of about 300-500 microns, thereby further supporting the bone healing side of the enthesis. For the side of the patch system to be positioned closer to the tendon, i.e., the top or tendon side of the patch, the patch system may define a pore size of about 100-300 microns, thereby providing an environment that is conducive for tenocyte colonization and integration between bone and tendon.

The spacing and orientation of the various filaments that define the patch layers can be selected so as to optimize stimulation of the desired tissue regeneration. In like measure, the orientation of the filament direction can be selected so as to guide the direction of the regenerated tissue. For example, the top layer (tendon side) of the patch system may be advantageously fabricated/manufactured with longitudinal filaments to guide Sharpey fiber tendon growth and attachment to bone, thereby beneficially creating an enthesis oriented with the direction of resultant forces acting on the tendon.

Additional features, functions and benefits of the disclosed patch system and associated method will be apparent from the description which follows.

BRIEF DESCRIPTIONS OF THE FIGURES

To assist those of skill in the art in making and using the disclosed systems and methods, reference is made to the accompanying figures, wherein.

DESCRIPTION OF EXEMPLARY EMBODIMENTS

As noted above, the present disclosure provides an interpositional patch system and associated method that includes physical/mechanical feature(s) produced from a citrate-based composite biomaterial to aid enthesis regeneration. The physical/mechanical feature(s) are generally arranged/deployed as a gradient architecture through the patch system via a plurality of layers. For the patch surface to be clinically positioned closer to the bone site, the physical/mechanical feature(s) are designed to create/define a porosity of about 300-500 microns, thereby further supporting the bone healing side of the enthesis, and for the side of the patch system to be positioned closer to the tendon, i.e., the top or tendon side of the patch, the patch system defines a pore size of about 100-300 microns, thereby providing an environment that is conducive for tenocyte colonization and integration between bone and tendon. The spacing and orientation of the various filaments that define the patch layers can be selected so as to optimize stimulation of the desired tissue regeneration. In like measure, the orientation of the filament direction can be selected so as to guide the direction of the regenerated tissue.

Figure 1:
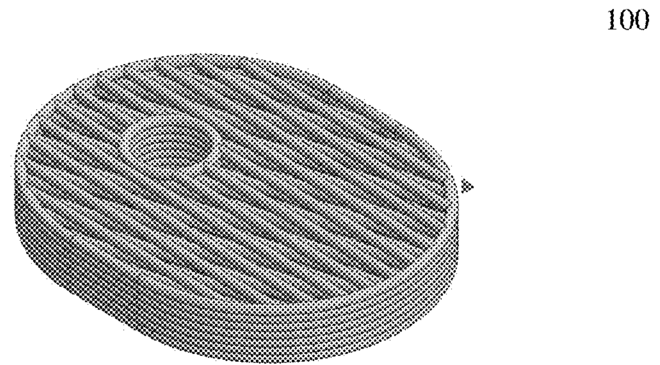
FIG. 1 shows a representation of an assembled format of an exemplary patch system.
Figure 2:
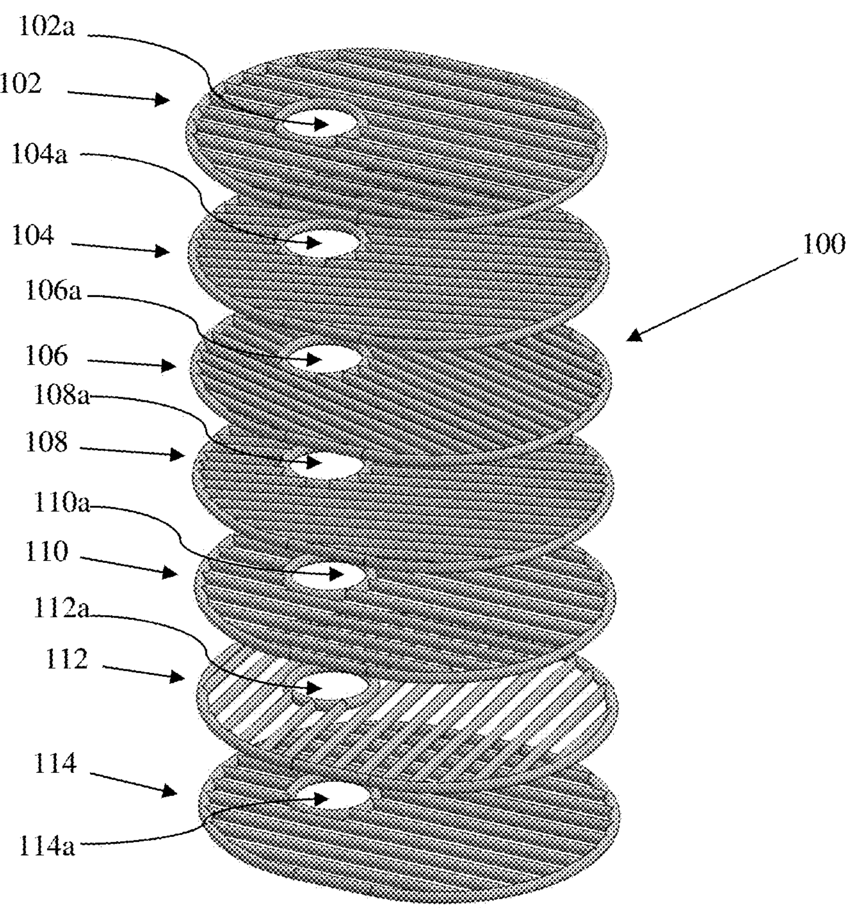
FIG. 2 shows a representation of an exploded format of an exemplary patch system.

A first exemplary embodiment of the disclosed patch system is schematically depicted in FIG. 1 (assembled) and FIG. 2 (exploded).

As shown in FIGS. 1 and 2, patch system 100 comprises a plurality of patch layers 102, 104, 106, 108, 110, 112, 114 that, in the assembled configuration shown in FIG. 1, define a stacked configuration with substantially common exterior edges. Patch system 100 defines a substantially oval outer geometry. Adjacent layers are in contacting relationship. At least one aperture/passage is defined in the face of each patch layer (apertures 102*a*-114*a*) and, when assembled, the apertures/passages 102*a*-114*a* are substantially aligned to define a contiguous passage through patch system 100. The disclosed contiguous passage provides room/space for formation of natural host tissues (i.e., bone-enthesis-tendon). Within a patch, a plurality of passages are generally provided and the sizing of the passages are generally designed in size and shape to promote/accommodate formation and entry of desired tissue. For example, larger passage spacing is generally advantageous for formation of osseous tissue and smaller passage spacing is generally advantageous for tendon tissue, with a gradient in between to form transition from bone to tendon (enthesis).

Figure 3:
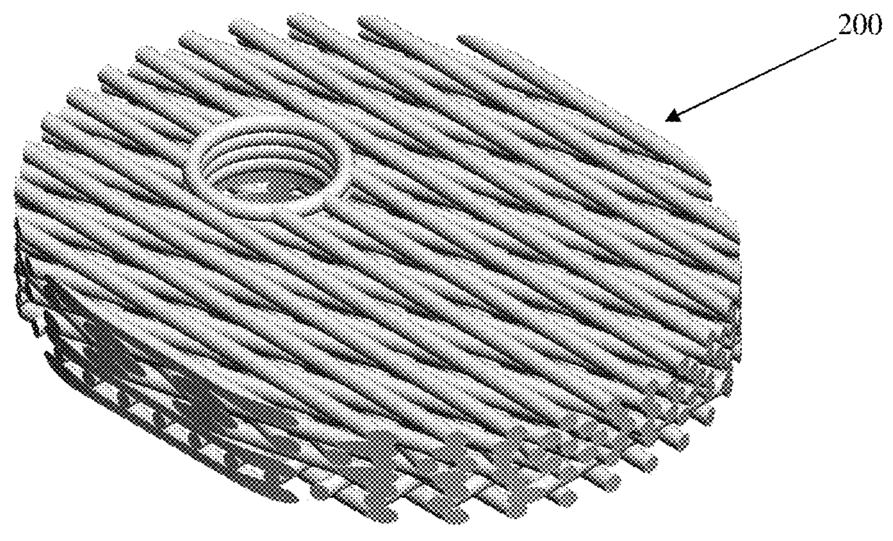
FIG. 3 shows a representation of an exemplary patch system that includes an open/unbounded perimeter.

In the depicted embodiment of FIGS. 1 and 2, each of layers 102-114 defines a solid perimeter, e.g., formed by the extruded polymer; however, in alternative embodiments, the outer perimeter of the layer(s) may be open, i.e., unbounded, to facilitate cellular diffusion of patch materials and bodily fluids (see FIG. 3).

As best seen in FIG. 2, the filaments that define the respective layers are generally oriented in non-aligned axes such that a crossing of fibers exists between each adjacent layer. Of note, it is not necessarily the case that the filament alignment is different for each layer relative to other layers in exemplary embodiments of the present disclosure, but only that adjacent layers are defined by fibers that are not aligned with the fibers of adjacent layer(s). Typical fiber diameters range between 1 micron and 5 microns, but the present disclosure is not limited by or to such exemplary fiber dimensions.

Patch system 100 thus defines a gradient architecture across layers 102-114. The patch surface/layer to be clinically positioned closer to the bone site, a porosity of about 300-500 microns is generally defined, thereby further supporting the bone healing side of the enthesis, and the layer/surface to be positioned closer to the tendon, i.e., the top or tendon side of the patch, a pore size of about 100-300 microns is generally defined, thereby providing an environment that is conducive for tenocyte colonization and integration between bone and tendon. The spacing and orientation of the various filaments that define the patch layers can be selected so as to optimize stimulation of the desired tissue regeneration, and the orientation of the filament direction can be selected so as to guide the direction of the regenerated tissue.

In alternative embodiments of the disclosed patch system, alternative outer geometries/profiles may be chosen, i.e., geometries/profiles other than the oval design of patch system 100. For example, square or triangular geometries/profiles may be selected, although the present disclosure is not limited by or to any specific outer geometry/profile.

Exemplary patch system 100 includes seven (7) layers (102-114). However, the disclosed patch system is not limited by or to such exemplary implementation, and patch systems may be fabricated/implemented according to the present disclosure that include more or less than seven (7) layers. It is also contemplated according to the present disclosure that alternative fabrication methods may be employed that do not require fabrication of individual layers that are assembled in the manner shown in FIGS. 1 and 2, but instead provide a gradient effect across the thickness of the patch system through alternative manufacturing techniques.

As noted above, alternative embodiments of the present disclosure may include layer(s) that define an open/unbounded perimeter. FIG. 3 schematically depicts an exemplary patch system 200 that includes an open/unbounded perimeter.

The beneficial clinical attributes of the disclosed patch systems are further enhanced by the chemistry of the material used to fabricate the patch system. Specifically, the disclosed patch system is that is primarily composed of citrate-based polymers, a key metabolite in the creation of energy in the Krebs Cycle. In exemplary embodiments, the disclosed patch system is fabricated, in whole or in part, from a biocomposite constituted of citrate polymer and a bioceramic filler.

Figure 4A:
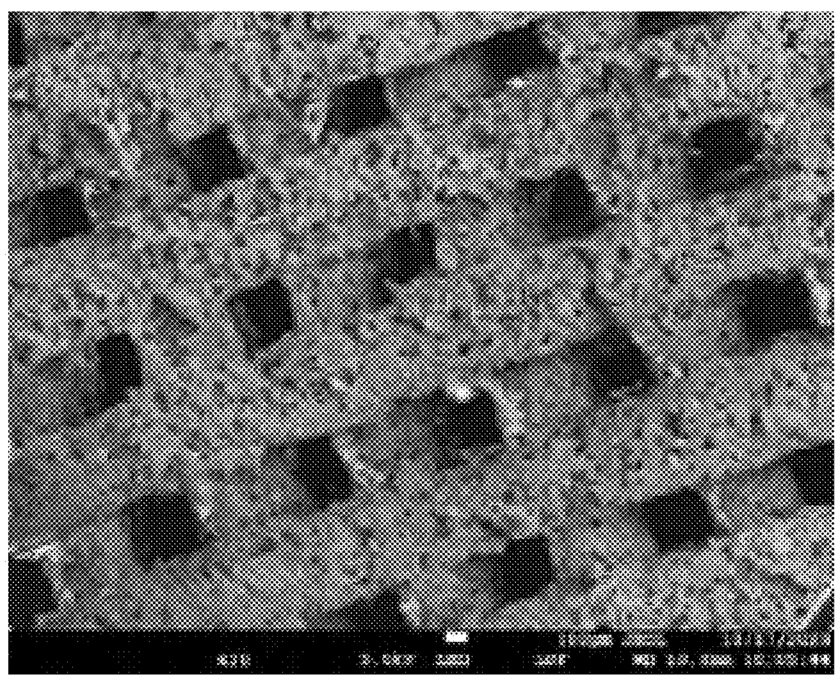
FIG. 4A shows a scanning electron microscopy image of a patch system from the top down showing the porous fiber structure.
Figure 4B:
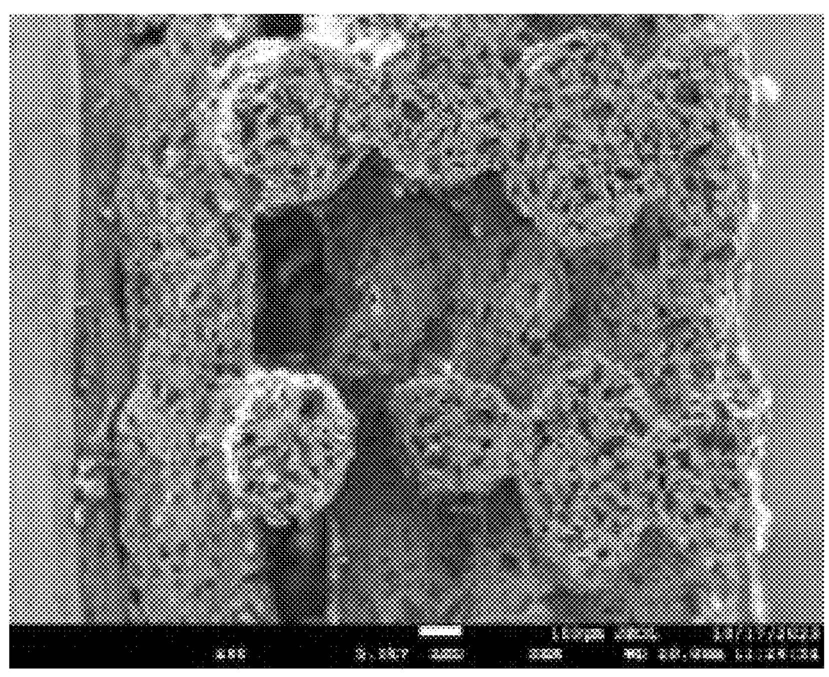
FIG. 4B shows a scanning electron microscopy image showing a cross-section of a patch system.
Figure 4C:
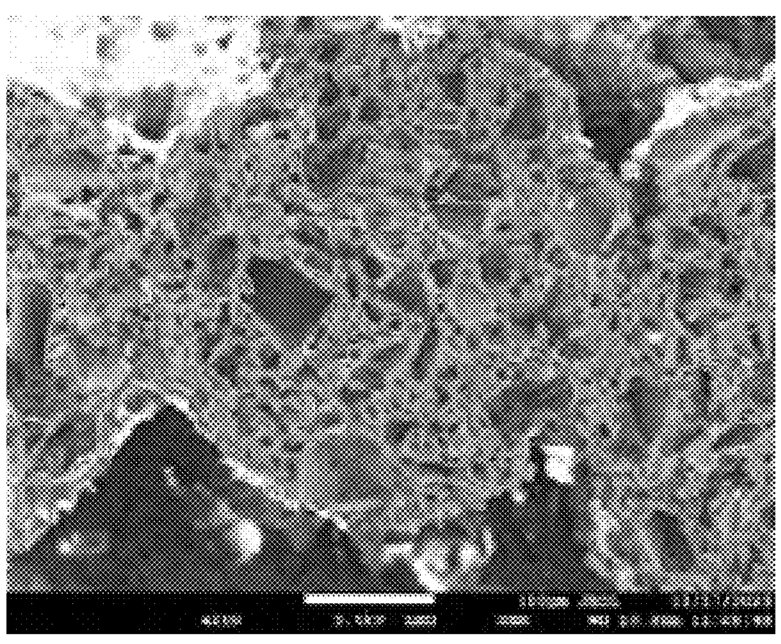
FIG. 4C shows an enlarged section of the scanning electron microscopy image of a cross-section of a patch system to demonstrate the submicron porosity of the filaments.

Manufacture of the disclosed patch systems may be undertaken by a 3D printing modality, e.g., utilizing a technique such as extrusion of the biocomposite in a process termed Fused Deposition Modeling (FDM). In FDM, the biocomposite is extruded from a nozzle and a pattern is created and layered to create a 3D object. Utilizing FDM allows multiple filaments to be created in various diameters and spacing between the filaments to create pockets (pores) that can be changed as the spacing or filament diameter is changed. The filament itself can be either solid or semi-porous by adding a solvent or sacrificial component that can be removed later by various methods to create microporosity within the filament. The microporosity of the filament can be altered and can aid in controlling degradation rate and provide further mechanical features for cell attachment. (see, e.g., FIGS. 4A-4C).

The FDM method allows multiple patterns to be produced which can be changed, layer by layer, to create features that allow optimized biological integration and cell signaling. Although the manufacture of the implant has been described using FDM 3D printing, this layered method can be created by also using casting techniques or other additive manufacturing processes, such as laser printing or with binder jetting techniques.

The citrate polymer can possess various types of bioceramic fillers, such as bioglass, hydroxyapatite (HA), tricalcium phosphate (TCP), calcium sulfate or various other ceramic fillers in either particle or fiber forms. The bioceramic filler can take the form of blends or mixes of bioceramic materials, including specifically the exemplary bioceramic filler materials identified herein. The above-mentioned bioceramic materials may be used in various concentrations to best align with clinical requirements. For example, the bioceramic filler may be incorporated into the fibers/layers at a level of 0% to 50% by weight. For example, bioceramic may be included at a lesser level, e.g., 25% by weight, in the "tendon" layer, at a greater level, e.g., 35% by weight, at intermediate layer(s), and at a highest level, e.g., 45% by weight, in the "bone" layer. The variable bioceramic levels are not limited by or to such exemplary weight percentages, but may be varied based on clinical requirements as noted above. The biomaterial can also be loaded and/or conjugated with various proteins or peptides to increase cellular response.

In exemplary embodiments of the present disclosure, the disclosed patch system may be used in rotator cuff repair.

Exemplary patch system design parameters for rotator cuff repair may include the following:

Patch Thickness: 2 mm to 5 mm

Patch Dimensions: 5 mm×5 mm

Fiber/strut diameter: 1 micron or greater

Porosity: 300-500 microns on bone side; 100-300 microns on tendon side

Degradation profile: 12-18 months

Bioceramic HA, TCP, calcium sulfate and mixtures thereof

Gradient layering: Tendon side—lower ceramic content; bone side—higher ceramic content Although the present disclosure has been described with reference to exemplary embodiments and implementations of the disclosed patch system/method, the present disclosure is not limited by or to such exemplary embodiments/implementations.

The invention claimed is:

1. A patch system for use in musculoskeletal repair, comprising:

a multi-filament patch that defines a patch thickness, the multi-filament patch fabricated, in whole or in part, from a composition that includes a citrate polymer and a bioceramic filler;

wherein the multi-filament patch defines a porosity gradient across the patch thickness based on at least one of (i) variations in filament diameter and (ii) variations in filament spacing.

2. The patch system according to claim 1, wherein the multi-filament patch is defined by a plurality of patch layers.

3. The patch system according to claim 2, wherein the patch layers are formed from a plurality of fibers.

4. The patch system according to claim 3, wherein first fibers in a first patch layer are non-aligned relative to second fibers in a second, adjacent patch layer.

5. The patch system according to claim 1, wherein each of the patch layers define an aperture, and wherein the apertures of the patch layers are substantially aligned when the patch is assembled.

6. The patch system according to claim 1, wherein the multi-filament patch defines a solid perimeter.

7. The patch system according to claim 1, wherein the multi-filament patch defines an open or unbounded perimeter.

8. The patch system according to claim 1, wherein the bioceramic filler is selected from the group consisting of bioactive glass, hydroxyapatite (HA), tricalcium phosphate (TCP), calcium sulfate, and combinations thereof.

9. The patch system according to claim 1, wherein the multi-filament patch is formed from a plurality of patch layers, and wherein the bioceramic filler level varies across the patch layers.

10. The patch system according to claim 1, wherein the multi-filament patch defines a first patch layer that is configured to be positioned adjacent a bone, and a second patch layer that is configured to be positioned adjacent a tendon, and wherein the bioceramic filler is at a greater level in the first patch layer as compared to the second patch layer.

11. The patch system according to claim 1, wherein the multi-filament patch defines a first patch layer that is configured to be positioned adjacent a bone, and a second patch layer that is configured to be positioned adjacent a tendon, and wherein the porosity is greater for the first patch layer as compared to the second patch layer.

12. The patch system according to claim 11, wherein the pore size of the first patch layer is 300-500 microns, and the pore size of the second patch layer is 100-300 microns.

13. The patch system according to claim 1, wherein the degradation profile of the patch is 12-18 months.

14. The patch system according to claim 1, wherein the multi-filament patch is fabricated from a plurality of fibers, and wherein the diameter of the fibers is 1 micron to 5 microns.

15. The patch system according to claim 1, wherein the patch thickness is 2 mm to 5 mm.

16. The patch system according to claim 1, wherein the multi-filament patch dimensions are 5 mm by 5 mm.

17. A patch system for use in musculoskeletal repair, comprising:

a multi-filament patch that defines a patch thickness, the multi-filament patch fabricated, in whole or in part, from a composition that includes a citrate polymer and a bioceramic filler;

wherein the multi-filament patch defines a porosity gradient across the patch thickness based on at least one of (i) variations in filament diameter and (ii) variations in filament spacing;

wherein the multi-filament patch is defined by of a plurality of patch layers;

wherein each of the plurality of patch layers defines an aperture and the apertures of the plurality of patch layers are substantially aligned when the multi-filament patch is assembled.

18. The patch system according to claim 17, wherein each of the apertures is bounded.

19. A patch system for use in musculoskeletal repair, comprising:

a multi-filament patch that defines a patch thickness, the multi-filament patch fabricated, in whole or in part, from a composition that includes a citrate polymer and a bioceramic filler;

wherein the multi-filament patch defines a porosity gradient across the patch thickness based on at least one of (i) variations in filament diameter and (ii) variations in filament spacing;

wherein the multi-filament patch is defined by of a plurality of patch layers, and wherein first fibers in a first patch layer are non-aligned relative to second fibers in a second, adjacent patch layer.

20. The patch system of claim 19, wherein the first fibers in the first patch layer and the second fibers in the second, adjacent patch layer are in non-parallel alignment relative to each other.

21. The patch system of claim 19, wherein the first fibers in the first patch layer and the second fibers in the second, adjacent patch layer are perpendicularly aligned relative to each other.

* * * * *